United States Patent
Nakaigawa et al.

(10) Patent No.: US 11,061,034 B2
(45) Date of Patent: Jul. 13, 2021

(54) BLOOD BIOMARKER FOR USE IN EVALUATION OF EFFECT OF DRUG THERAPY ON KIDNEY CANCER

(71) Applicant: PUBLIC UNIVERSITY CORPORATION YOKOHAMA CITY UNIVERSITY, Yokohama (JP)

(72) Inventors: Noboru Nakaigawa, Yokohama (JP); Daiki Ueno, Yokohama (JP); Masahiro Yao, Yokohama (JP)

(73) Assignee: PUBLIC UNIVERSITY CORPORATION YOKOHAMA CITY UNIVERSITY, Yokohama (JP)

(*) Notice: Subject to any disclaimer, the term of this patent is extended or adjusted under 35 U.S.C. 154(b) by 277 days.

(21) Appl. No.: 15/768,192

(22) PCT Filed: Oct. 11, 2016

(86) PCT No.: PCT/JP2016/080084
§ 371 (c)(1),
(2) Date: May 16, 2018

(87) PCT Pub. No.: WO2017/065127
PCT Pub. Date: Apr. 20, 2017

(65) Prior Publication Data
US 2018/0321246 A1 Nov. 8, 2018

(30) Foreign Application Priority Data
Oct. 14, 2015 (JP) .............................. JP2015-202614

(51) Int. Cl.
*G01N 31/00* (2006.01)
*G01N 33/53* (2006.01)
*G01N 33/574* (2006.01)
*G01N 33/50* (2006.01)
*A61K 45/00* (2006.01)

(52) U.S. Cl.
CPC ....... *G01N 33/57438* (2013.01); *G01N 33/50* (2013.01); *G01N 33/53* (2013.01); *G01N 33/574* (2013.01); *A61K 45/00* (2013.01); *G01N 2333/98* (2013.01)

(58) Field of Classification Search
None
See application file for complete search history.

(56) References Cited

U.S. PATENT DOCUMENTS

| | | |
|---|---|---|
| 2008/0220530 A1 | 9/2008 | Bahn et al. |
| 2009/0209431 A1 | 8/2009 | Villoch et al. |
| 2009/0263842 A1 | 10/2009 | Krizman |
| 2013/0259847 A1 | 10/2013 | Vishnudas et al. |
| 2015/0031048 A1 | 1/2015 | Van Eyk et al. |

FOREIGN PATENT DOCUMENTS

| | | |
|---|---|---|
| JP | 2008-542742 A | 11/2008 |
| JP | 2009-511028 A | 3/2009 |
| JP | 2014-517300 A | 7/2014 |
| JP | 2015-513370 A | 5/2015 |
| JP | 2015-519876 A | 7/2015 |
| WO | WO 2012/164026 A1 | 12/2012 |

OTHER PUBLICATIONS

Zhu et al. (Journal of Experimental & Clinical Cancer Research 2012, pp. 1-6) (Year: 2012).*
Zhu et al. (Journal of Experimental & Clinical Cancer Research 2012, paaes 1-6) (Year: 2012).*
He et al. (J Dig Dis 2011, 12:131-137) (Year: 2011).*
Bande et (Invest Ophthalmol Vis Sci. 2012;53:62-67) (Year: 2012).*
Sitaram et al. (Int. J. Cancer Res. vol. 125, pp. 783-790, 2009) (Year: 2009).*
Baumunk et al. (World J. Urol. vol. 31, pp. 1191-1196, 2013). (Year: 2013).*
Yanez et al. (Curr Oncol Rep. vol. 14, No. 3, Jun. 2012, pp. 1-15). (Year: 2012).*
Pastore et al. (Disease Markers, vol. 2015, Article ID 251403, pp. 1-9). (Year: 2015).*
International Search Report, issued in PCT/JP2016/080084, dated Dec. 20, 2016.
Written Opinion of the International Searching Authority, issued in PCT/JP2016/080084, dated Dec. 20, 2016.
He et al., "Serum DJ-1 as a diagnostic marker and prognostic factor for pancreatic cancer", Journal of Digestive Diseases, vol. 12, 2011, pp. 131-137 (7 pages).
Supplementary European Search Report, dated May 13, 2019, for European Application No. 16855381.
Trivedi et al., "The antioxidant protein PARK7 plays an important role in cell resistance to Cisplatin-induced apoptosis in case of clear cell renal cell carcinoma", European Journal of Pharmacology, vol. 784, 2016, pp. 99-110(12 pages).
Mackeigan, Jeffrey P., et. al.. "Proteomic Profiling Drug-Induced Apoptosis in Non-Small Cell Lung Carcinoma: Identification of RS/DJ-1 and RhoGDIalpha1." Cancer Research, Oct. 15, 2003, vol. 63, pp. 6928-6934.
Naour. Franc ois Le, et al., "Proteomics-based Identification of RS/DJ-1 as a Novel Circulating Tumor Antigen in Breast Cancer1," Clinical Cancer Research, Nov. 2001, vol. 7, pp. 3328-3335.

* cited by examiner

*Primary Examiner* — Lisa V Cook
(74) *Attorney, Agent, or Firm* — Birch, Stewart, Kolasch & Birch, LLP

(57) ABSTRACT

Disclosed are methods for determining the efficacy of a pharmacotherapy drug for kidney cancer using a blood test. The methods include the evaluation of the effect of a drug therapy for the treatment of kidney cancer by measuring the PARK7 level in a blood sample taken from a patient with kidney cancer who receives the drug therapy for the treatment of kidney cancer. An increased PARK7 level indicates that the drug therapy is not effective. Moreover, by using the blood PARK7 level as an indicator, the efficacy of a candidate substance for a therapeutic agent for kidney cancer can also be determined.

6 Claims, 2 Drawing Sheets
Specification includes a Sequence Listing.

BLOOD BIOMARKER FOR USE IN EVALUATION OF EFFECT OF DRUG THERAPY ON KIDNEY CANCER

This application is a U.S. National Phase of PCT/JP2016/080084, filed Oct. 11, 2016, which claims priority under 35 U.S.C. § 119(e) to Application No. 2015-202614 filed in Japan, on Oct. 14, 2015, the entire contents of all of which are expressly incorporated by reference into the present application.

TECHNICAL FIELD

The present invention relates to a blood biomarker for evaluation of the effect of a drug therapy for kidney cancer.

BACKGROUND ART

Incidence of kidney cancer in Japan is 7 to 8 in every one hundred thousand people, and is rising year after year. Surgical resection is the gold standard treatment of kidney cancer. However, in approximately 30% of all patients with kidney cancer, kidney cancer will metastasize to different sites, which is called advanced cancer. Drug therapy or immunotherapy is applied to patients with advanced cancer in whom surgery is not feasible.

The pharmacotherapy drugs currently available for patients with kidney cancer are molecularly targeted drugs, which are categorized into tyrosine kinase inhibitors (TKIs) and mTOR inhibitors. The efficacy of such pharmacotherapy drugs for kidney cancer have been determined by the rate of tumor shrinkage examined with images obtained by CT scanning or the like. However, some drugs rarely cause tumor shrinkage, which makes the evaluation of the effects of the drugs difficult. For example, in TKI therapy, the response rate (tumor shrinkage rate) is not as outstanding as that from conventional anticancer drug therapy, and a rate of tumor shrinkage of 30% or higher, which is calculated based on CT imaging, is associated with only approximately 10 to 30% of the cases of kidney cancer treated by that therapy. Moreover, even in patients on whom the drug therapy is effective, several months are often needed to allow any tumor shrinkage to be detected by CT scanning. Therefore, currently, administration of that type of pharmacotherapy drugs is continued until a clear response is observed by CT imaging.

TKI therapy causes various side effects different from those induced by conventional anticancer drugs, including hypertension, diarrhea, general malaise, hand-foot syndrome and the like, which is considered problematic. If the therapeutic effect of a drug therapy on a patient can be determined early after the start of treatment, then the treatment which has evaluated as an ineffective therapy practically producing no positive effects on the patient is not continued, which can result in improved prognosis and/or QOL of patients. However, disadvantageously, evaluation of the effect by CT scanning takes longer time as described above. Furthermore, frequent CT scanning is difficult from the viewpoint of radiation exposure, which may result in missing the timing to change a pharmacotherapy drug. If a specific blood test method (blood biomarker) that reflects the pathology of kidney cancer can be established, more frequent examination is possible without the risk of radiation exposure and evaluation of the effect at the required timing is possible even at an institution equipped with no CT scanner. However, currently such a blood biomarker does not exist.

The DJ-1 gene was isolated as a novel oncogene by Ariga et al., at Hokkaido University in 1997, which is cooperatively involved in neoplastic transformation of cells. Subsequently, the same gene was isolated as PARK7, a causative gene for familial Parkinson's disease, in 2003 and is currently called PARK7/DJ1. The PARK7/DJ1 gene is reportedly involved in protection from oxidative stress due to reactive oxygen, transcriptional regulation, and regulation of protease activity and mitochondrial function, as well as its relationship with breast cancer and non-small cell lung cancer is also indicated (Non-Patent Documents 1 and 2). Two reports, one by Sitaram el al., in 2009 (Non-Patent Document 3) and the other by Baumunk et al., in 2013 (Non-Patent Document 4), are related to the relationship of PARK7/DJ1 and kidney cancer (renal carcinoma).

In Non-Patent Document 3, expression of PARK7/DJ-1, c-Myc and hTERT was analyzed by RT-PCR. The authors reported that expression of PARK7/DJ-1 was increased in order of normal tissue (n=49)<papillary renal cell carcinoma tissue (n=23)<renal clear cell carcinoma tissue (n=153) and renal cell carcinoma (RCC) tissue, and concluded that any correlation between the expression of DJ-1, c-Myc and hTERT genes and the prognosis was not observed.

In Non-Patent Document 4, expression of PDK-1 and PARK7/DJ1 was analyzed in 91 RCC cases by RT-PCR. The authors reported that expression of PARK7/DJ1 was detected in both normal renal tissue and RCC tissue but there was no difference in expression level between them, and concluded that any clinical or pathological correlation was not observed.

As described above, correlation between the progression or activity of kidney cancer and the expression of PARK7 in the cancer tissue has been negatively reported, and, furthermore, neither correlation between blood PARK7 level and the therapeutic effect of a drug therapy for kidney cancer nor usefulness of PARK7 as a blood biomarker for evaluation of the effect of a drug therapy for kidney cancer is recognized at all.

PRIOR ART DOCUMENTS

Non-Patent Documents

Non-Patent Document 1: Le Naour el al., Clin. Cancer Res. 7, 3328-3335, 2001.
Non-Patent Document 2: MacKeigan et al., Cancer Res. 63, 6928-6934, 2003.
Non-Patent Document 3: Sitaram et al., Int. J. Cancer, 125, 783-790, 2009.
Non-Patent Document 4: Baumunk et al., World J Urol, 31, 1191-1196, 2013.

SUMMARY OF THE INVENTION

Problems to be Solved by the Invention

An object of the present invention is to provide a means whereby the efficacy of a pharmacotherapy drug for kidney cancer can be easily determined by a blood test.

Means for Solving the Problems

The inventors intensively made an effort to screen such a protein that its concentration in blood is decreased by TKI therapy in a responder group, in which long-term progression-free survival was obtained, and increased by the same therapy in a non-responder (progression) group, to find that PARK7 was a potent blood biomarker for evaluating the efficacy of TKIs and mTOR inhibitors. The inventors further found that, because the pathology (activity) of kidney cancer was reflected by the level of PARK7 in blood, the blood PARK7 level could be used for evaluation of the therapeutic effects of not only molecularly targeted therapeutic agents such as TKIs and mTOR inhibitors but also various pharmacotherapy drugs for kidney cancer including a novel therapeutic agent for kidney cancer that will be put into practical use in future, and also for evaluation of the therapeutic effect of a candidate substance for use as the novel therapeutic agent. Thus, the present invention has been completed.

That is, the present invention provides a method of assisting the evaluation of the effect of a drug therapy, the method comprising measuring a PARK7 level in a blood sample taken from a patient with kidney cancer who receives the drug therapy for the treatment of kidney cancer, wherein an increased PARK7 level indicates that the drug therapy is not effective. The present invention also provides use of PARK7 as a blood biomarker for evaluation of the effect of a drug therapy for kidney cancer. The present invention further provides a blood biomarker composed of PARK7 for evaluation of the effect of a drug therapy for kidney cancer. The present invention still further provides a method of assisting the evaluation of the effect of a candidate substance for a therapeutic agent for kidney cancer, the method comprising measuring a PARK7 level in blood samples taken from a test subject with kidney cancer before and after administration of the candidate substance, wherein the candidate substance is determined to potentially be effective in the treatment of kidney cancer when the PARK7 level in the blood sample taken after the administration is decreased relative to the PARK7 level in the blood sample taken before the administration.

Effect of the Invention

According to the present invention, a blood biomarker capable of evaluating the effect of a drug therapy for kidney cancer was provided for the first time. The blood PARK7 level of a patient who receives a drug therapy is useful as data for use in evaluation of the therapeutic effect of a pharmacotherapy drug being used and serves as a great aid for evaluation of the effect of the drug therapy by a physician. Because the therapeutic effect can be determined by the blood PARK7 level at a very early stage after the start of treatment, the effect of the drug therapy can be determined earlier by the blood PARK7 level than by examining whether tumor has been shrunk or not by CT scanning. Moreover, according to the present invention, because the therapeutic effect can be determined with a small volume of blood sample, more frequent monitoring is possible without concerns about radiation exposure, which is also advantageous for quick evaluation of the therapeutic effect. Since a blood test can be easily performed even at an institution equipped with no CT scanner, the present invention is highly convenient. The present invention enables early detection of loss of therapeutic effects and allows one to take countermeasures against it, such as changing the therapeutic agent, as well as the present invention enables the evaluation of therapeutic effects at appropriate timing. Thus, the number of patients with kidney cancer who continue a drug therapy practically producing no therapeutic effects is decreased, from which improvement of prognosis in patients with kidney cancer as well as improvement of QOL and a positive effect on medical economy can be expected. Because the blood PARK7 level reflects the activity of kidney cancer, it can be used for evaluation of the effect of a candidate substance for a therapeutic agent for kidney cancer, as well as for evaluation of the effects of various pharmacotherapy drugs. By using the blood PARK7 level for evaluation of the effect of a candidate substance for a therapeutic agent, in the clinical study of a new therapeutic agent for human kidney cancer, for example, the effect of the corresponding new therapeutic agent can be quickly evaluated. The present invention also contributes to the development of a new therapeutic agent for kidney cancer.

MODE FOR CARRYING OUT THE INVENTION

Figure 1:
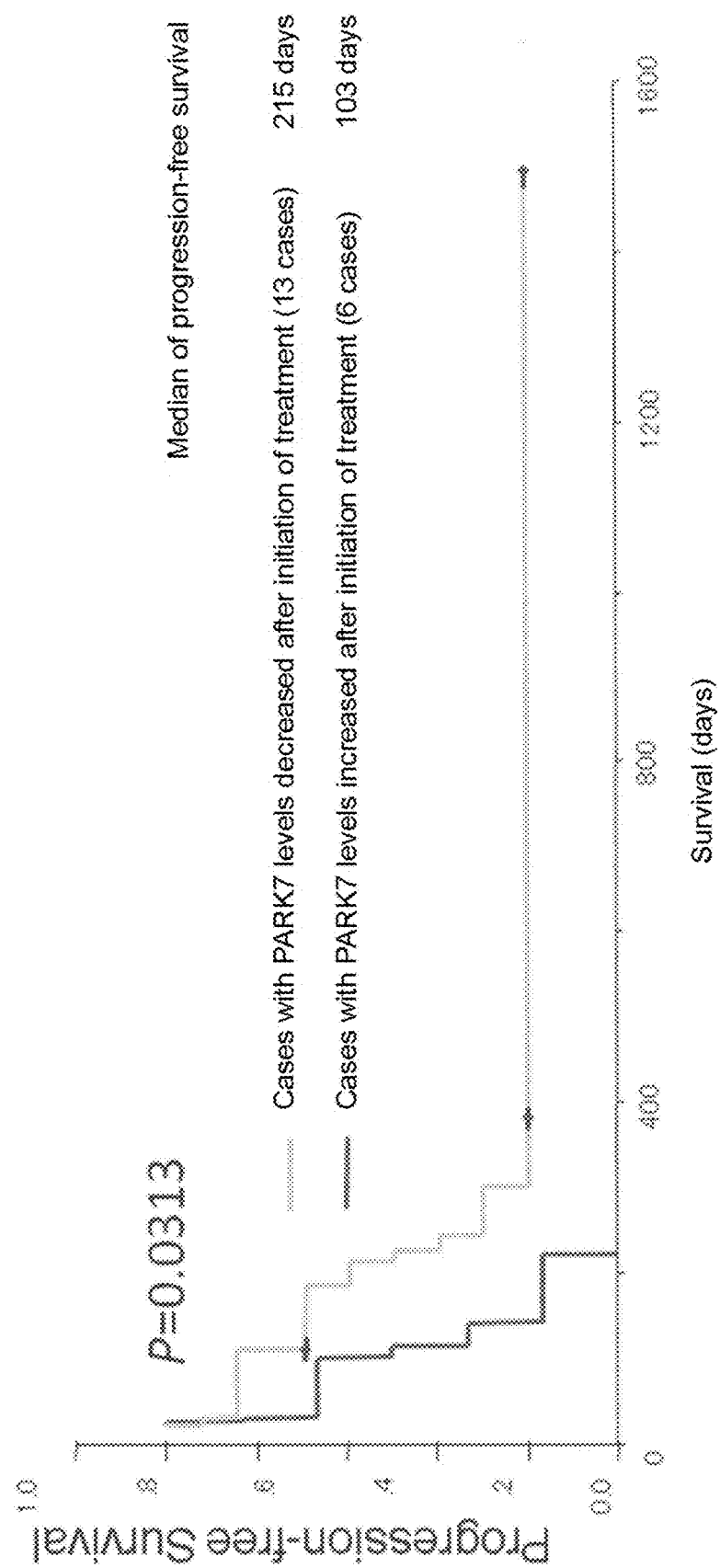
FIG. 1 shows the result of measuring the progression-free survival rate in kidney cancer patient groups with decreased blood PARK7 levels and with increased blood PARK7 levels at two weeks after the start of TKI administration.

The amino acid sequence shown in SEQ ID NO: 2 is the amino acid sequence of human PARK7. Multiple mRNA sequences are registered in the database at NCBI as transcription variants 1, 2, and X1 (accession Nos. NM_007262.4, NM_001123377.1, and XM_005263424.2, respectively), any of which encodes a PARK7 protein with an identical amino acid sequence. The base sequence registered under the accession No. NM_007262.4 is shown in SEQ ID NO: 1 as an exemplary mRNA sequence from the PARK7 gene.

The target patient of the present invention is a patient with kidney cancer (particularly, advanced kidney cancer, such as metastatic kidney cancer and unresectable kidney cancer) who receives a drug therapy, typically a human patient.

The term "kidney cancer" in the present invention has the same meaning as "renal cell carcinoma", including renal clear cell carcinoma, papillary renal cell carcinoma, chromophobe renal cell carcinoma, collecting duct carcinoma, and the like.

The term "drug therapy" includes therapy with various agents that exert therapeutic effects on kidney cancer, and also includes, for example, immunotherapy with cytokines or the like. The medicine used in the drug therapy is not particularly limited, and includes various agents such as small molecule compounds, molecularly targeted drugs, nucleic acid therapeutics, antibody therapeutics, peptide therapeutics, and the like. Pharmacotherapy drugs for kidney cancer currently in practical use are molecularly targeted drugs, which are broadly classified into tyrosine kinase inhibitors (TKIs), such as sunitinib and sorafenib, which inhibit vascularization, and mTOR protein inhibitors, which suppress cancer growth mainly by inhibiting the enzyme that regulates cancer growth. Any pharmacotherapy drug belonging to either category can be evaluated for its effect according to the present invention because the change in blood PARK7 level reflects the effect of a medicine being used, as described in Examples below. Moreover, recently, immune checkpoint inhibitors such as anti-PD-1 antibody and anti-PD-L1 antibody gain attention in the field of cancer therapy. In Japan and in foreign countries, immune checkpoint inhibitors are in clinical trials as therapeutic agents for various cancers such as kidney cancer, malignant melanoma, and non-small cell lung cancer, and some of them have already been approved also in Japan. They are expected to also be approved and practically used in future as therapeutic agents for kidney cancer. Such new therapeutic agents for kidney cancer as immune checkpoint inhibitors will also be subjects of the evaluation of therapeutic effects according to the present invention. Because the blood PARK7 level reflects the activity of kidney cancer and, thus, the change in the activity of kidney cancer can be evaluated by the change in blood PARK7 level, the present invention based on the blood PARK7 level is not limited to the above indicated examples but can be used for evaluation of the effects of various pharmacotherapy drugs for kidney cancer.

The blood sample includes a whole blood sample, a plasma sample, and a serum sample. A blood sample used in the present invention may be, for example, a plasma sample or a serum sample. Or, the blood sample may be a plasma sample.

The collection of blood samples is continued during the period in which the patient receives drug administration. For the comparison purpose, blood samples are preferably collected prior to and/or at the start of drug therapy. Blood samples are usually collected every a few or several weeks, but the timing of blood sampling may be changed appropriately according to the conditions of a patient, symptoms, and the like.

The PARK7 level of a sample can be determined by measuring the abundance of the PARK7 protein or its fragment in the sample. The means of measuring the PARK7 level in a sample is not particularly limited as long as it is a means capable of measuring polypeptides. Examples of the means of measuring polypeptides include immunoassay, mass spectrometry, and the like, and immunoassay is preferably used in the present invention because it does not need a large-scale machinery and equipment and its measuring operations are easy to perform. Polyclonal and monoclonal antibodies that can detect PARK7 are known and are also commercially available. Moreover, because the amino acid sequence of PARK7 and the base sequence encoding the same are known as described above, an anti-PARK7 antibody or an antigen-binding fragment thereof that specifically recognizes PARK7 may be prepared by a commonly used method such as the hybridoma method.

An anti-PARK7 polyclonal antibody can be obtained by, for example, immunizing a non-human animal with the full-length PARK7 protein or its fragment comprising an appropriate partial region together with an adjuvant as necessary, collecting blood from the non-human animal to obtain an antiserum, and purifying the polyclonal antibody of interest in the antiserum. The immunization is typically carried out multiple times over several weeks to raise the antibody titer in the immunized animal. The antibody in the antiserum can be purified, for example, by fractionation based on ammonium sulfate precipitation or anion chromatography, affinity column purification, and the like.

An anti-PARK7 monoclonal antibody can be obtained by, for example, immunizing a non-human animal with the full-length PARK7 protein or an appropriate fragment of the protein, collecting antibody-producing cells such as splenocytes or lymphocytes from the animal, preparing hybridomas by the fusion of those cells with myeloma cells, screening a hybridoma clone capable of producing an antibody that binds to PARK7, and culturing the hybridoma clone and collecting the culture supernatant to obtain the antibody of interest.

The full-length PARK7 protein or a fragment thereof used for the immunization of a non-human animal can be produced based on the information including the known base sequence and amino acid sequence of PARK7, which are also indicated in the Sequence Listing, by commonly used methods such as chemical synthesis, genetic engineering technique, and the like.

Specific examples of the chemical synthesis method include the Fmoc method (the fluorenylmethyloxycarbonyl method), tBoc method (the t-butyloxycarbonyl method), and the like. Moreover, the synthesis may also be carried out using various commercially available peptide synthesizers by a commonly used method. In the case of chemical synthesis, a desired polypeptide can be synthesized based only on its amino acid sequence.

In cases where the full-length PARK7 protein or its fragment is produced by genetic engineering technique, it may be produced by, for example, amplifying a desired region of the PARK7 cDNA from a human cDNA library, integrating the amplified region into an appropriate vector, expressing a polypeptide corresponding to the amplified region in an appropriate expression system, and recovering the expressed polypeptide. The vectors and various expression systems (bacterial expression system, yeast cell expression system, mammalian cell expression system, insect cell expression system, cell-free expression system, and the like) to be used are also well known, and various vectors, host cells, reagents, and kits are commercially available. Therefore, those skilled in the art can select and use appropriate ones. Human-derived cultured cells are also commercially available or distributed and can be easily obtained.

The "antigen-binding fragment" may be any antibody fragment as long as it retains the binding activity to the antigen (antigen-antibody reactivity) of the original antibody. Specific examples of the antigen-binding fragment include, but are not limited to, Fab. $F(ab')_2$, scFv, and the like. Fab and $F(ab')_2$ fragments can be obtained, as known well, by treating a monoclonal antibody with a protein degradation enzyme such as papain or pepsin. The production method for scFv (single chain fragment of variable region, single-chain antibody) is also well known. A scFv fragment can be obtained, for example, by extracting mRNA from the hybridoma produced as described above to prepare single-stranded cDNA; carrying out PCR using immunoglobulin H chain-specific and L chain-specific primers to amplify the immunoglobulin H chain gene and L chain gene from the single-stranded cDNA; connecting the amplified fragments by a linker; adding thereto appropriate restriction enzyme sites; introducing it into a plasmid vector; transforming *E. coli* bacteria with the plasmid vector to express the scFv fragment; and recovering the scFv fragment from the *E. coli* bacteria.

The immunoassay per se is a well-known commonly used method. Immunoassays are categorized based on the format of reaction into sandwich immunoassay, competitive immunoassay, agglutination immunoassay. Western blot, and the like, while immunoassays are categorized based on the label to be used into enzyme immunoassay, radioimmunoassay, fluorescent immunoassay, and the like. In the present invention, any immunoassay method capable of quantitative detection of the protein of interest may be used. For example, a sandwich method such as, but not limited to, sandwich ELISA may be preferably used.

In the sandwich method, an anti-PARK7 antibody that binds to PARK7 is immobilized on a solid phase (immobilized antibody), and allowed to react with a sample. After washing, a labeled anti-PARK7 antibody which can bind to PARK7 in parallel with the immobilized antibody (typically, an anti-PARK7 antibody that binds to PARK7 at a different site from that of the immobilized antibody) is allowed to react with the solid phase. After washing, the labeled antibody bound to the solid phase is measured. Both the immobilized antibody and the labeled antibody may be polyclonal or monoclonal antibodies. Antigen-binding fragments of the respective antibodies may also be used instead of the antibodies.

The measurement of the labeled antibody can be carried out by measuring the signal from the labeling substance. The method of measuring the signal is appropriately selected depending on the type of the labeling substance. In the case of an enzyme label, for example, a substrate for the enzyme is added to the reaction system, and the intensity of color or luminescence produced by the enzyme reaction may be measured with an absorptiometer or a luminometer. The amount of PARK7 in a blood sample can be determined as follows: standard samples containing various known concentrations of PARK7 are immunologically assayed using an anti-PARK7 antibody or an antigen-binding fragment thereof, and the correlation between the amount of signal from the label and the concentrations of PARK7 in the standard samples is plotted to generate a standard curve, and the same procedure is performed on a blood sample containing an unknown concentration of PARK7 to determine the amount of signal from the label, and the determined value of signal is applied to the standard curve to obtain the concentration of PARK7. The measured value is simply required to be compared with a previously measured value from the same patient, and therefore, the calculation of an absolute concentration value is not essential. The change in PARK7 level may also be evaluated by the comparison between detected signal values.

When monoclonal antibodies are used as both an immobilized antibody and a labeled antibody, whether the combination of monoclonal antibodies is preferable or not can be easily examined by actually performing an immunoassay. Optionally, the recognition sites of the antibodies may be identified to determine if they recognize different epitopes. The identification of antibody recognition sites can be performed by a commonly used method well known in the art. Briefly, for example, the corresponding antigen. PARK7, is partially digested with a protein degradation enzyme such as trypsin, and a solution containing the partial digests is filtered through an affinity column of an immobilized antibody, which is to be examined for its recognition site. Thereafter, the digests are allowed to bind to the antibody, and the bound digests are then eluted from the column and analyzed by a conventional mass spectrometry, and thereby the recognition site of the antibody can be identified.

The blood PARK7 level varies depending on the size of a kidney cancer, and a larger tumor size is associated with a higher blood level of PARK7, while the blood level of PARK7 is not very different between normal subjects and patients with a small tumor size. Thus, it is difficult to set up an absolute cut-off value that can be commonly applied to overall patients with kidney cancer. However, a change in blood PARK7 level is observed regardless of the size of a kidney cancer, where the level of PARK7 in blood is maintained low when a drug therapy is effective, and is increased when the drug therapy is ineffective or loses its effect. Therefore, in the present invention, whether the PARK7 level has been increased or not is determined by examining the change in PARK7 level in an individual and comparing the measured value with a previously measured value from the identical patient.

Whether the PARK7 level has been increased or not is determined by comparing the measured value at least with the last measurement value. That is, it can be determined mainly by comparison with the last measurement value, and additionally by considering the tendency of change from the second last measurement or an earlier measurement as necessary. If the blood PARK7 level is decreased or maintained low, a medicine being used can be determined to be therapeutically effective and, therefore, the use of the same medicine may be continued with monitoring the progress. If the blood PARK7 level is sharply increased, it may indicate the possibility of rapid progression of kidney cancer, and it is desirable to immediately replace a medicine being used with another type of medicine. If the blood PARK7 level tends to be gradually increased, a medicine being used may be immediately replaced with another type of medicine, or replacement of the medicine may be considered after performing the next measurement earlier than scheduled and reconfirming the increasing tendency. If the blood PARK7 level is not particularly changed from the level at the start of therapy with the medicine, the medicine can be less effective. In such a case, the next measurement may be performed earlier than scheduled as necessary, and then the replacement of the medicine being used may be considered, taking the extent of side effects into account.

Because the blood PARK7 level reflects the activity of kidney cancer, the effect of a candidate substance for a therapeutic agent for kidney cancer can be evaluated by using the blood PARK7 level as an indicator. In the evaluation of the effect of a candidate substance, the candidate substance is administered to a test subject with kidney cancer. The test subject is a human or non-human mammal. If the test subject is a human, it is primarily envisioned that evaluation of the effect of the candidate substance is carried out in clinical trials. The non-human mammal may be, for example, a kidney cancer model to which renal carcinoma cells have been transplanted. Blood samples are collected from the test subject before and after administration of the candidate substance, and the PARK7 level is measured in these blood samples. The blood sample may be collected once or multiple times after the administration. If the blood PARK7 level after the administration is decreased relative to the blood PARK7 level before the administration, the candidate substance can be determined to potentially be effective for the treatment of kidney cancer.

Examples

The present invention will be more specifically described below by way of examples. However, the present invention is not limited to the examples below.

1. Correlation Between the Change in Blood Concentration of PARK7 and the Prognosis in Patients with Kidney Cancer being Treated with a TKI From 19 patients with advanced renal cell carcinoma who had been receiving administration of a TKI (tyrosine kinase inhibitor) as a therapeutic agent for kidney cancer, blood samples were collected at the start of dosing and at week 2 after the first dosing. Plasma was separated therefrom, and the PARK7 level in the plasma was measured. A commercially available sandwich ELISA kit (Cyclex Co., Ltd) was used for the measurement, and the color developed by the reaction between HRP enzyme label and its substrate substance was detected by a luminometer. The PARK7 standard attached in the kit was used to prepare reference samples for generation of a standard curve. The concentration of PARK7 in the plasma samples were calculated by applying measured values to the standard curve. When the change in plasma PARK7 level was evaluated by comparing the calculated PARK7 concentrations or comparing the values detected by the luminometer, the plasma PARK7 level at week 2 after the first dosing relative to that at the start of TKI administration was decreased in 13 cases, and it was increased in 6 cases. Then, the progression-free survival in the groups of cases with decreased levels and of cases with increased levels was investigated.

The result is shown in FIG. 1. A significant difference in progression-free survival was observed between the 13 cases with PARK7 levels decreased as compared with that at the start of treatment and the 6 cases with PARK7 levels increased as compared with that at the start of treatment, and the progression-free survival rate was significantly higher in the group of cases with decreased PARK7 levels than in the other group (P=0.0313). The median of progression-free survival was 215 days in the group of cases with decreased levels, while it was 103 days in the group of cases with increased levels. Accordingly, it was confirmed that the blood PARK7 level enabled the evaluation of the therapeutic effect of a drug therapy for kidney cancer at a stage as early as week 2 after the start of treatment.

2. Correlation Between the Change in Blood Concentration of PARK7 and the Prognosis in Patients with Kidney Cancer being Treated with an mTOR Inhibitor (Temsirolimus)

A change in blood PARK7 concentration was observed during treatment in four patients with kidney cancer who began to receive administration of mTOR inhibitor. The blood PARK7 concentration was measured as a concentration of plasma PARK7 with the commercially available ELISA kit in the same manner as in 1, described above, and the change in blood PARK7 level was evaluated by comparing values detected by a luminometer.

The therapeutic effect of the mTOR inhibitor was clinically evaluated by FDG PET/CT. Kidney cancer progression was evaluated by FDG PET/CT, in parallel with the measurement of blood PARK7 concentration. FDG is an agent composed of glucose and a positron-emitting nuclide introduced thereto, and it has almost the same behavior in the body as glucose. Since glucose is highly accumulated in tumor regions when a cancer is highly active, the activity of the cancer can be evaluated by examining the accumulation of FDG.

Figure 2:
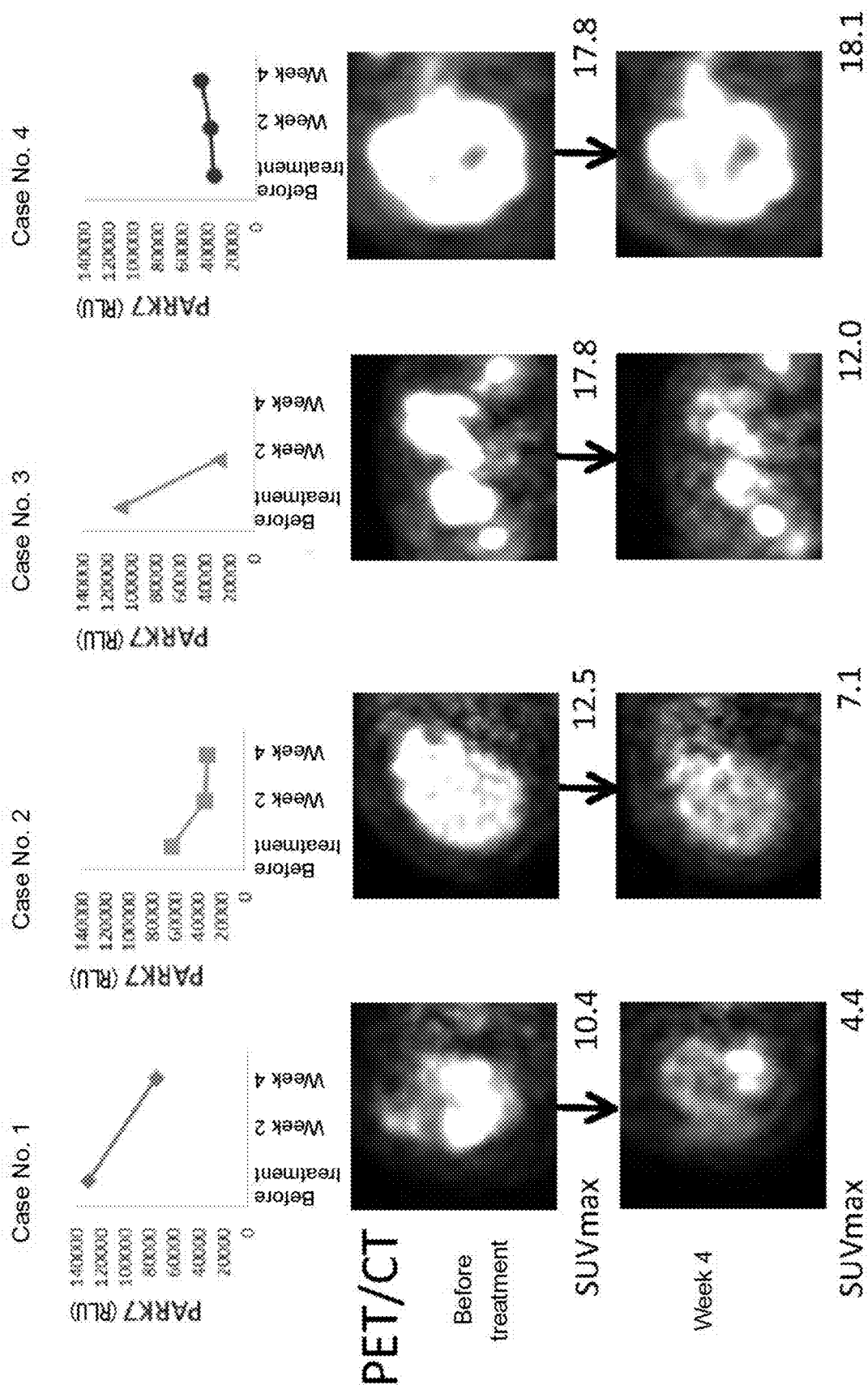
FIG. 2 shows the results of measuring the change in blood PARK7 level by FLISA and of examining the activity of kidney cancer by PET/CT in four patients with kidney cancer, to whom an mTOR inhibitor has started to be administered.

The result is shown in FIG. 2. The SUVmax values indicated below the respective images are semi-quantified values of FDG accumulation. In all of the three cases (Case Nos. 1 to 3) in whom the concentration of PARK7 in blood was decreased during the mTOR inhibitor therapy, the evaluation by PET/CT demonstrated a decreased accumulation of FDG, indicating a decreased activity of the cancer, that is, the achievement of therapeutic effects. On the other hand, in one case (Case No. 4) in whom the concentration of PARK7 was increased, no change in accumulation of FDG was observed, indicating the ineffectiveness of the therapy. Accordingly, it was suggested that the therapeutic effect can be determined based on the change in blood PARK7 concentration, also for an mTOR inhibitor-type therapeutic agent for kidney cancer.

The invention claimed is:

1. A method of evaluating the effect of a drug therapy for the treatment of a kidney cancer, the method comprising
administering the drug therapy for the treatment of the kidney cancer to a patient with the kidney cancer;
measuring a parkinson protein 7 (PARK7) level in first and second blood samples taken from the patient, the first sample being collected from the patient prior to collection of the second sample; and
comparing the PARK7 level measured in the first sample to the PARK7 level measured in the second sample, wherein an increased PARK7 level measured in the second sample compared to the first sample indicates that the drug therapy is not effective for the treatment of the kidney cancer in the patient.

2. The method according to claim 1, wherein the blood sample is a plasma or serum sample.

3. A method of evaluating of the effect of a candidate substance as a therapeutic agent for a kidney cancer, the method comprising
administering the candidate substance to a subject with the kidney cancer,
measuring a PARK7 level in blood samples taken from the subject with the kidney cancer before and after administration of the candidate substance,
comparing the PARK7 levels measured in the blood samples, and
identifying the candidate substance as a therapeutic agent for the kidney cancer if the PARK7 level in the blood sample taken after the administration of the candidate substance is decreased relative to the PARK7 level in the blood sample taken before the administration of the candidate substance.

4. The method according to claim 3, wherein the blood sample is a plasma or serum sample.

5. The method according to claim 1, further comprising changing the drug therapy to another drug therapy if the PARK7 level measured in the second sample is greater than the PARK7 level measured in the first sample.

6. The method according to claim 3, further comprising administering the candidate substance identified as the therapeutic agent to the subject to treat the kidney cancer.

* * * * *

SEQUENCE LISTING

```
<160> NUMBER OF SEQ ID NOS: 2

<210> SEQ ID NO 1
<211> LENGTH: 979
<212> TYPE: DNA
<213> ORGANISM: Homo sapiens
<220> FEATURE:
<221> NAME/KEY: CDS
<222> LOCATION: (164)..(733)

<400> SEQUENCE: 1
tgagtctgcg cagtgtgggg ctgagggagg ccggacggcg cgcgtgcgtg ctggcgtgcg      60
ttcattttca gcctggtgtg gggtgagtgg tacccaacgg gccggggcgc cgcgtccgca     120
ggaagaggcg cggggtgcag gcttgtaaac atataacata aaa atg gct tcc aaa      175
                                                Met Ala Ser Lys
                                                  1 aga gct ctg gtc atc ctg gct aaa gga gca gag gaa atg gag acg gtc      223
Arg Ala Leu Val Ile Leu Ala Lys Gly Ala Glu Glu Met Glu Thr Val
  5                  10                  15                  20 atc cct gta gat gtc atg agg cga gct ggg att aag gtc acc gtt gca      271
Ile Pro Val Asp Val Met Arg Arg Ala Gly Ile Lys Val Thr Val Ala
                 25                  30                  35 ggc ctg gct gga aaa gac cca gta cag tgt agc cgt gat gtg gtc att      319
Gly Leu Ala Gly Lys Asp Pro Val Gln Cys Ser Arg Asp Val Val Ile
             40                  45                  50 tgt cct gat gcc agc ctt gaa gat gca aaa aaa gag gga cca tat gat      367
Cys Pro Asp Ala Ser Leu Glu Asp Ala Lys Lys Glu Gly Pro Tyr Asp
         55                  60                  65 gtg gtg gtt cta cca gga ggt aat ctg ggc gca cag aat tta tct gag      415
Val Val Val Leu Pro Gly Gly Asn Leu Gly Ala Gln Asn Leu Ser Glu
     70                  75                  80
```

```
tct gct gct gtg aag gag ata ctg aag gag cag gaa aac cgg aag ggc      463
Ser Ala Ala Val Lys Glu Ile Leu Lys Glu Gln Glu Asn Arg Lys Gly
85              90                  95                  100 ctg ata gcc gcc atc tgt gca ggt cct act gct ctg ttg gct cat gaa      511
Leu Ile Ala Ala Ile Cys Ala Gly Pro Thr Ala Leu Leu Ala His Glu
            105                 110                 115 ata ggt ttt gga agt aaa gtt aca aca cac cct ctt gct aaa gac aaa      559
Ile Gly Phe Gly Ser Lys Val Thr Thr His Pro Leu Ala Lys Asp Lys
        120                 125                 130 atg atg aat gga ggt cat tac acc tac tct gag aat cgt gtg gaa aaa      607
Met Met Asn Gly Gly His Tyr Thr Tyr Ser Glu Asn Arg Val Glu Lys
                135                 140                 145 gac ggc ctg att ctt aca agc cgg ggg cct ggg acc agc ttc gag ttt      655
Asp Gly Leu Ile Leu Thr Ser Arg Gly Pro Gly Thr Ser Phe Glu Phe
    150                 155                 160 gcg ctt gca att gtt gaa gcc ctg aat ggc aag gag gtg gcg gct caa      703
Ala Leu Ala Ile Val Glu Ala Leu Asn Gly Lys Glu Val Ala Ala Gln
165                 170                 175                 180 gtg aag gct cca ctt gtt ctt aaa gac tag agcagcgaac tgcgacgatc        753
Val Lys Ala Pro Leu Val Leu Lys Asp
                185 acttagagaa acaggccgtt aggaatccat tctcactgtg ttcgctctaa acaaaacagt    813 ggtaggttaa tgtgttcaga agtcgctgtc cttactactt ttgcggaagt atggaagtca    873 caactacaca gagatttctc agcctacaaa ttgtgtctat acatttctaa gccttgtttg    933 cagaataaac agggcattta gcaaactaaa aaaaaaaaaa aaaaaa                   979

<210> SEQ ID NO 2
<211> LENGTH: 189
<212> TYPE: PRT
<213> ORGANISM: Homo sapiens

<400> SEQUENCE: 2

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
                20                  25                  30

Val Thr Val Ala Gly Leu Ala Gly Lys Asp Pro Val Gln Cys Ser Arg
            35                  40                  45

Asp Val Val Ile Cys Pro Asp Ala Ser Leu Glu Asp Ala Lys Lys Glu
        50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160
```

```
Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185
```